United States Patent [19]

Fuierer

[11] Patent Number: 5,244,387
[45] Date of Patent: Sep. 14, 1993

[54] MEASURING PROBE TO DETECT POCKET DEPTH OF A TOOTH HOLDING APPARATUS

[76] Inventor: Dieter Fuierer, Happinger Strasse 74, 8200 Rosenheim, Fed. Rep. of Germany

[21] Appl. No.: 904,961

[22] Filed: Jun. 26, 1992

[51] Int. Cl.⁵ .............................................. A61C 19/04
[52] U.S. Cl. ..................................... 433/72; 128/776
[58] Field of Search ........................ 433/72; 128/776; 33/514

[56] References Cited

U.S. PATENT DOCUMENTS

| | | | |
|---|---|---|---|
| 4,883,425 | 11/1989 | Zimble | 128/776 |
| 5,022,856 | 6/1991 | Zimble | 128/776 |

FOREIGN PATENT DOCUMENTS

| | | | |
|---|---|---|---|
| 0286067 | 4/1988 | European Pat. Off. | 128/776 |
| 84/03143 | 2/1984 | PCT Int'l Appl. | 128/776 |
| 89/01314 | 2/1989 | PCT Int'l Appl. | 128/776 |

*Primary Examiner*—John J. Wilson
*Attorney, Agent, or Firm*—Oblon, Spivak, McClelland, Maier & Neustadt

[57] ABSTRACT

A measuring probe to detect pocket depth of a tooth holding apparatus by inserting a feeler as far as the bottom of the gum pocket. A light beam is generated which can be moved relative to the feeler. A detector detects reflected light beams by being irradiated with the reflected light beams while the detector outputs the detected signals to an evaluator. The evaluator evaluates the output signals to determine the pocket depth.

10 Claims, 1 Drawing Sheet

MEASURING PROBE TO DETECT POCKET DEPTH OF A TOOTH HOLDING APPARATUS

BACKGROUND OF THE INVENTION

1. Field of the Invention

The present invention is directed to a measuring probe for detecting the pocket depth of a tooth holding apparatus.

2. Discussion of the Background

A measuring probe for detecting the pocket depth of a tooth holding apparatus is known from, for example, EPA 0286 067, where the pocket depth is measured by inserting a feeler as far as the bottom of the gum pocket and subsequently moving a light beam as far as an upper rim of the gum under the control of an operator. When a transfer switch is operated, a value corresponding to an actual angular position of the light beam generator is evaluated as the measure of the pocket depth. Such a design using a movable light beam has an advantage over other systems which use probing elements which are slid on or in the feeler in that the measuring operation can be effected substantially without effort, since no forces have to be raised to move the probing element. In addition, problems due to the obstruction of the sliding guidance rendering the movement of the probe element difficult or even blocking the probe element are eliminated. Of course, the movement of the light beam that is controlled by the operator on the rim of the gum requires an accurate visual inspection in order to avoid any measuring errors. This feature correspondingly requires the concentration of the operator. In addition, this method of measurement is difficult in regions where the teeth are difficult to see.

SUMMARY OF THE INVENTION

Accordingly, one object of the present invention is to provide a novel measuring probe which overcomes these drawbacks and which enables an accurate measurement of the pocket depth without any difficulties.

A measuring probe according to the present invention which achieves this objective has a detector, which is irradiated by a light beam during its movement. The detector emits subsequently an output signal, whose pattern is representative of the modulation of the light beam caused by the region that is probed. This modulation is induced by the difference between the absorption or attenuation of the light in the region of the gum and the regions of the tooth or the feeler that is exposed above the gum. From the pattern of the output signal of the detector, the evaluator can compute the height from the bottom of the feeler tip, i.e., the bottom of the pocket, to the gum upper rim, and thus the pocket depth. This determined output value can then be permanently registered and/or displayed on a display screen.

Further, according to the present invention, the detector may be attached to the handle of a measuring probe, so that all active components, such as the light beam generator, the detector and, optionally, the evaluator, can be housed in the handle. In this case, the region of the feeler, which makes contact with the patient, has no active voltage carrying components or mechanically moving components, so that the safety of the patient is not negatively affected, and the functionality of the measuring probe is also not subjected to any disturbances. In this case, the detector detects the light, which is reflected by the region irradiated by the light beam and whose reflecting portions in the region of the gum are less, as a rule, than the portions reflected by the exposed tooth or feeler regions.

Further, by attaching a measurement scale to the feeler according to the present invention, light reflections, which are detected by the detector, may be generated pulse-like only by the exposed reflection fields when the light beam is swept over a measurement scale. The lower segments of the scale of the feeler inserted into the gum pocket are covered by the gum so that no light pulses are reflected by these segments. Therefore, the evaluation can be done in a simple manner by counting the number of light pulses detected by the detector, whereby the difference between the number of the maximum possible light reflections, i.e., the number of existing reflecting surfaces of the measurement scale and the number of detected light pulses or reflections represents the respective pocket depth.

As a further feature of the present invention, the light beam can also be moved sideways next to the feeler, so that a commercially available probe head without any special properties can be used as the feeler. The pocket depth is evaluated hereby by evaluating the varying reflectivity of the gum and the exposed tooth regions, where the output signal of the detector in the region of the upper gum rim abruptly changes. By detecting the position of this indicial response in the detector output signal the pocket depth can be determined.

As a further feature, a laser diode may be used as the light beam generator which provides the advantage that a light beam with a relatively high light intensity and small beam diameter can be obtained, where additionally the focusing measures are significantly simpler than with conventional light sources.

Also, the light beam generator, which may be formed preferably by a laser diode, may be mounted to be stationary which has the advantage that the attachment can be realized in a very simple manner, and no swivel mechanism to swivel the light beam generator (for the movement of the light beam) is necessary. Such a swivel mechanism can also be associated with the disadvantage that the swivel movement becomes more difficult with increasing life span and/or the reference positions for bottommost and upper swivel positions can change owing to deposits of dust or abrasion particles or the like. The conversion of the light beam emitted by the stationary light beam generator into a moving light beam may be effectuated by a revolving mirror, which can be designed as a metallized mirror, but which may also preferably rotate continuously. Owing to the continuous rotation of the revolving mirror, the light beam is swiveled constantly only in one direction, for example from top to bottom, and thus scans only in one direction. This facilitates the evaluation of the signal, since the time characteristics of the detector output signal represents the unidirectional spatial characteristics of the surface scanned by the light beam.

Also, according to the present invention, only one single control push-button may be used so that the operation can be facilitated by one hand, since only one single push-button has to be operated. As a further benefit, the power consumption of the measuring probe is also reduced, since only during pocket depth measurement, i.e., after depressing the push-button once, the light beam generator and the electric components must be activated, whereas depressing the push-button twice leads to a shutdown of these components while simultaneously retaining the determined pocket depth measurement value.

As an alternative, it can also be advantageous to have the deflecting mirror (revolving mirror) rotate continuously and also to keep in continuous operation the light beam generator after the start of the deflecting mirror. In this case no startup waiting intervals at the start of measurement are necessary; and in addition, during every measurement pause a system test can be conducted, thus testing, e.g., whether the probe tip is dirty.

The measuring probe operation can also be made very simple, since only one control push-button has to be operated.

As a further feature, one or more push-buttons may be attached to the measuring probe. In this case, the revolving mirror may rotate continuously. By depressing a push-button, the continuous measuring process is taken over in the evaluator. By means of various push-button sequences similar to Morse code and/or through the use of several push-buttons, commands can also be given to the evaluator.

Thus, the measuring probe according to the present invention enables a certain automatic measurement, during which the operator has only to insert the feeler into the gum pocket. An operator-side adjustment of the scanning light beam with specific visual monitoring is not necessary. Thus, regions of the teeth that are difficult to inspect can also be checked in a simple and reliable manner. In addition, no separate probing element which must be moved mechanically at or in the feeler is necessary, so that an operator can work with simple feelers that can be thoroughly and completely cleaned and sterilized in a very simple manner.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
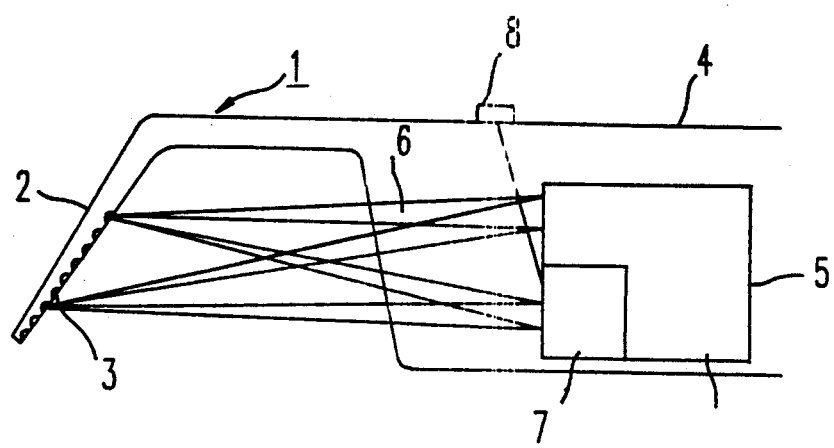
FIG. 1 is a side view of a first embodiment of the measuring probe.

Referring now to the drawings, wherein the reference numerals designate identical or corresponding parts throughout the several views, and more particularly to FIG. 1 thereof, which shows an embodiment of a measuring probe 1 which exhibits a feeler 2, which can be integrated into the measuring probe 1, but which is also preferably removable from the measuring probe in order to replace the feeler 2 and/or to clean and sterilize it.

The feeler 2 features a measurement scale 3, which exhibits a plurality of small reflecting surfaces in succession in the longitudinal direction of the feeler 2. The reflecting surfaces are separated from each other by narrow non-reflecting regions or regions that do not reflect light beams in the direction of a detector 7. The mean distance between reflecting surfaces can be, e.g., 0.2 mm.

A light beam generator 5 is disposed in the handle 4 of the measuring probe 1 and generates a light beam 6, which strikes the measurement scale 3 and which moves along the scale. The light beam generator 5 can be attached in the handle 4 so as to swivel relative to the movement of the light beam. However, it is preferable to attach light beam generator 5 stationarily and, in this case, to utilize a movable light beam deflecting element in the form of a revolving mirror to cause the light beam 6 to scan the measurement scale 3. The light beam generator 5 can exhibit a conventional light source with preceding focusing optics to focus the light beam in the region of the feeler 2, but contains preferably a laser diode, which generates a light beam of small diameter and high focus with adequate light intensity by means of simple imaging optics (e.g., a lens).

The light beam deflecting element, which is an element in the light beam generator 5, can also be designed as an electroplated mirror, which sets the light beam into a cyclically alternating upward and downward motion (cycling movement) along the feeler 2. Preferably, however, a revolving mirror is used that rotates continuously at least during the measurement phases and is driven, for example, by a small electric motor. The revolving mirror can be formed by a simple metal plate, whose two surfaces exhibit adequate reflectivity or that can also be optionally metallized. As an alternative, a revolving polygonal mirror with three or more mirror surfaces arranged at identical angles can also be used. The use of a continuously rotating revolving mirror has the advantage that the light beam is moved continuously only in one direction over the region to be scanned, i.e., in the embodiment according to FIG. 1 over the measurement scale 3, a feature that facilitates the evaluation.

To detect the reflected light beam 6, detector 7 is used, which is designed preferably as a photo receiver. In the embodiment according to FIG. 1, the detector 7 is disposed in the handle 4 and receives the light beam 6 that is generated by the light beam generator 5 and reflected off the reflecting surfaces of the measurement scale 3.

Figure 2:
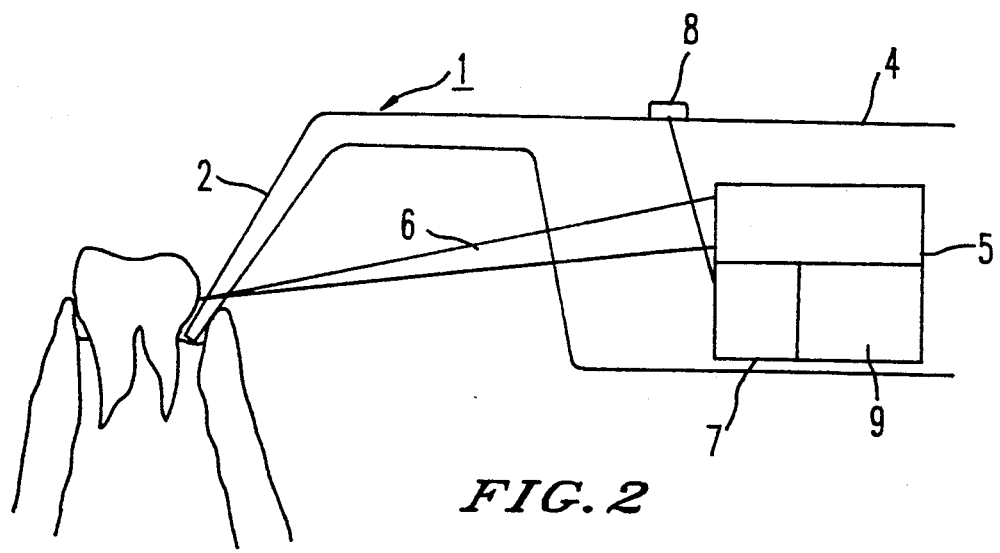
FIG. 2 is a side view of a further embodiment of the measuring probe.

When the light beam 6 is moved to scan the measurement scale 3, the individual reflecting surfaces generate light flashes or pulses, which are detected by the detector 7. When the feeler 2 is inserted as far as the bottom of the gum pocket, as is shown in FIG. 2, the lower reflecting surfaces of the measurement scale 3 are covered by the protruding gum rim. The number of covered reflecting surfaces is directly proportional to the pocket depth. If the light beam 6 generated during a measurement is moved to scan the measurement scale 3, the reflecting surfaces immersed into the pocket do not emit any reflecting light pulses. Only the exposed reflecting surfaces above the gum rim irradiated by the light beam 6, which is moved to scan the measurement scale 3, produce corresponding light flashes or pulses, whose number corresponds to the number of exposed reflecting surfaces.

The light flashes or pulses are converted into electric output pulses by the detector 7. By counting the number of detected light flashes or the number of output pulses, a conclusion can be drawn in a simple manner about the pocket depth. Preferably the number of detected light flashes or output pulses are counted downwardly starting from a specified value that corresponds to the maximum number of reflecting surfaces, whereby the reflecting count then directly represents the pocket depth. This counting operation can be done with an evaluator that is either also disposed in the measuring probe 1 or is attached externally and is connected to the measuring probe by means of electric lines.

As an alternative, the entire feeler 2, or at least the inside of the feeler can also be designed so as to reflect continuously, i.e., the feeler exhibits no measurement scale 3. In this case, when the light beam 6 sweeps over the feeler 2 immersed into the gum pocket, the detector output signals are produced that exhibit a high (or low) signal level when scanning the exposed reflecting feeler regions, whereas when scanning the gum the signal level is low (or high). In this case, the pocket depth can be measured by comparing the length of the segments with a high or low level or by detecting the position of the transition between the high and low signal level. Preferably the position and size of the angular region, in which the light beam is swiveled cyclically or rotatingly while scanning, is determined. Such a fixing of the scanning movement path is also logical in the embodiment according to FIG. 1 and in the embodiment according to FIG. 2 that is described in detail below, since then the risk of detecting interferences based on reflections from other regions of the mouth or from other segments of the measuring probe is low. In addition, the light beam scanning may start from a fixed reference point, namely the upper or lower limit of the pivotal region, which can serve as a reference point during evaluation of the signal. Preferably the scanning region of the light beam 6 is set in such a manner that it reaches from the feeler tip to the other end of the feeler 2 or sweeps exclusively the region of the measurement scale 3 when the measurement scale 3 is present.

Instead of designing a continuous or repeatedly interrupted reflecting surface on the feeler 2, it is also possible to affix the detector 3 directly on the feeler 2 in such a manner that it reaches from the feeler tip to a region of the feeler that corresponds to a maximum pocket depth. In this case the detector 7 is designed preferably by means of thin layer technology and is connected by means of signal lines to the evaluator disposed externally or in the measuring probe. In this case the optoelectric detector 7 emits output signals, whose signal amplitude or signal duration is representative of the degree to which the detector segment is irradiated by the light beam 6. Fabrication by means of thin layer technology has the advantage that the feeler 2 can still be subjected to high temperatures up to for example, 200° C., and cleaning and sterilization fluids without damaging the detector 7.

A further embodiment of the present invention is shown in FIG. 2, which differs from the embodiment according to FIG. 1 to the effect that the light beam 6 is guided sideways next to the feeler 2, preferably parallel to it, so that the light beam 6 scans the gum or tooth region lying next to the feeler 2. The region of movement of the cycling or rotating light beam 6 is hereby fixed preferably in such a manner that it reaches from the feeler tip to at least the region of maximum pocket depth. Scanning the region on the side of the feeler has the advantage that the feeler 2 does not need any special treatment, as for example metallizing, but rather can exhibit a conventional design. Since the tooth and the gum exhibit different reflectivities, the light intensity detected by the detector 7 with the feeler 2 inserted into the pocket while scanning the tooth is different from that during the scanning of the exposed gum region. This varying light intensity leads to a corresponding level change in the detector output signal during the transition from gum to tooth or vice versa. Consequently the pocket depth can be determined by detecting the position of the level change in the detector output signal. The resulting necessary reference values for specifying the chronological reference point are specified by a reference measurement system 9, which is disposed in the handle 4 of the measuring probe 1 and which can also serve simultaneously as the evaluator.

In the embodiments according to FIGS. 1 and 2, a push-button 8 is provided at a suitable spot on the outside of the handle 4. This push-button 8 can be used to start and terminate a measurement operation. When the push-button 8 is first operated, the measuring operation is started, thus switching on the light beam and also setting into motion the deflecting device, i.e., the deflecting mirror. At the same time the evaluation is also activated. Preferably the push-button 8 is thus operated by the operator when the feeler 2 is inserted completely into the gum pocket.

Upon a next operation of the push-button 8, the measurement is terminated again, thus preferably switching the light beam 6 off again and also bringing the deflecting mirror to a standstill. Furthermore, the measurement result obtained during the measurement phase is stored and/or displayed on a display screen. The process repeats itself with further push-button operations. With this concept it is possible to make due with only one single push-button 8, so that operating the measurement probe 1 is very simple.

During the continuous measurement phase the light beam 6 is moved at least once by means of the anticipated movement stroke. Preferably, however, the light beam 6 may sweep over the anticipated region of movement several times so that during one measurement phase for measuring a pocket depth several measurement results are obtained that are then processed in a statistical manner, e.g., by forming a mean value. This leads to an increase in accuracy when determining the depth of a pocket.

The evaluated signal may be evaluated and/or stored preferably by a computer, which simultaneously also prepares the necessary measurement record.

The measuring probe can also be designed in such a manner that it exhibits a push-button 8 which is a control push-button. In such a case, as an example, when push-button 8 is depressed once, a measurement value of pocket depth is transferred to the evaluator, when depressed twice a system test is conducted and when depressed a third time the last measurement value of pocket depth is erased.

The described measuring probe may work with a light generating means 5 with a rotating light beam or a scanning light beam that moves back and forth and enables an automatic pocket depth measurement without the necessity of movable probing bodies or the like.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United Stated is:

1. A measuring probe for detecting a pocket depth of a tooth holding apparatus comprising:
 a feeler which is inserted as far as a bottom of a gum pocket;
 a light beam generator for generating a light beam which can be moved relative to the feeler and which impinges on the feeler or gum regions lying next to the feeler;

a detector for detecting light signals reflecting off the feeler or the gum regions lying next to the feeler and outputting detection signals corresponding to the detected light signals; and an evaluator having a means for receiving the detection signals output from the detector and for evaluating a pocket depth of the feeler based on a level change in the detection signals output from the detector.

2. The measuring probe according to claim 1, wherein the detector is attached to a handle of the measuring probe.

3. The measuring probe according to claim 1, wherein the feeler comprises a measurement scale, which is scanned by the light beam during its movement and which comprises a plurality of small reflecting surfaces arranged in a direction of motion of the light beam, for reflecting the light beam to the detector.

4. The measuring probe according to either of claims 1 or 2, wherein the light beam is moved in such a manner that it is moved laterally next to the feeler.

5. The measuring probe according to any one of claims 1-3, wherein the light beam generator is a laser diode.

6. The measuring probe according to any one of claims 1-3 wherein the light beam generator is a laser diode and is attached stationarily in the measuring probe, and wherein the light beam generator comprises a revolving mirror for moving the light beam.

7. The measuring probe according to claim 6, wherein the revolving mirror rotates continuously.

8. The measuring probe according to claim 6, further comprising one or more push-buttons attached to the measuring probe, wherein the revolving mirror rotates continuously, wherein by depressing a push-button, the continuous measuring process is obtained in the evaluator, and wherein by means of various push-button sequences commands can be given to the evaluator.

9. The measuring probe according to any one of claims 1-3, further comprising a control push-button attached to the measuring probe which, when depressed once, starts generation and movement of the light beam and, when depressed twice, terminates the light beam generation.

10. The measuring probe according to any one of claims 1-3, further comprising a control push-button attached to the measuring probe which, when depressed once, a measurement value of the pocket depth is obtained, which, when depressed a second time, a system test is conducted and which, when depressed a third time, a last measurement value of the pocket depth is erased.

* * * * *